United States Patent [19]

Hoch et al.

[11] Patent Number: 4,660,580

[45] Date of Patent: Apr. 28, 1987

[54] PROCESS FOR THE PERMANENT SHAPING OF THE REGROWTH OF HAIR AND COMPOSITION THEREFORE

[75] Inventors: Dietrich Hoch, Pfungstadt; Theodor Wajaroff; Eugen Konrad, both of Darmstadt, all of Fed. Rep. of Germany

[73] Assignee: Wella Aktiengesellschaft, Darmstadt, Fed. Rep. of Germany

[21] Appl. No.: 642,670

[22] PCT Filed: Dec. 29, 1983

[86] PCT No.: PCT/EP83/00350

§ 371 Date: Aug. 10, 1984

§ 102(e) Date: Aug. 10, 1984

[87] PCT Pub. No.: WO84/02842

PCT Pub. Date: Aug. 2, 1984

[30] Foreign Application Priority Data

Jan. 19, 1983 [DE] Fed. Rep. of Germany ....... 3301515

[51] Int. Cl.$^4$ ............................................... A45D 7/00
[52] U.S. Cl. .......................................... 132/7; 424/70

[58] Field of Search .............................. 132/7; 424/70

Primary Examiner—Gregory E. McNeill
Attorney, Agent, or Firm—Michael J. Striker

[57] ABSTRACT

Process for a selective permanent shaping of the regrowth of hair, whereby the hair is at first treated with a liquid aqueous pretreatment substance, is rolled onto rollers, is treated with a aqueous reducing permanent shaping substance, rinsing, fixing it oxidatively and further treating it in a customaty manner, characterized in that the pretreatment and the permanent shaping substance is so selected that they form a separating layer at their contact face (uppermost layers of the rolled up hair) during contact, thus making an admixture of the pretreatment substance with the permanent substance more difficult or prevent it. Suitable combinations are for example: Pre=treatment substance containing either a high polymeric polycarboxylic acid polymer, whereby at least 25% Mol of these polymers consists of a free carboxylic acid group, or a water soluble aluminum salt in combination with an alkalic permanent shaping substance.

23 Claims, No Drawings

PROCESS FOR THE PERMANENT SHAPING OF THE REGROWTH OF HAIR AND COMPOSITION THEREFORE

The permanent hair shaping in the hitherto known processes occurs in two stages. At first the disulfide bridges of the hair keratin are cracked by means of a suitable reduction substance. Thereafter, the hair is brought into a new shape and is subsequently fixed in the new shape by treatment with a suitable oxidation substance by reestablishing the cracked disulfide compounds.

The compositions used for performing the first reducing process stage contain keratin reducing substance sulfite or certain mercapto compounds as the deforming effective substances, in particular thioglycolic acid, thiolactic acid also in form of their salts with inorganic bases or also thioglycerin or derivatives of these mercapto compounds. These compositions customarily are alkalically adjusted, so as to obtain a hair softening and thereby a rapid penetration of the keratin reducing substance into the hair keratin. Thereby, the required alkalinity is obtained, above all, by adding ammonia, organic amines, ammonium and alkali carbonate, ammonium and alkali hydrogen carbonate. The practical performance for a permanent shaping of human hair is carried out in the following general manner, in that the washed and towel dried hair is at first separated into a pluralities of batches and these batches are then wound onto rollers. After finishing the roller process the rollers are thoroughly moistened with the required amount of the permanent shaping agent. The rollers used for a permamnent wave have a diameter of about 3 to 13 millimeter, while for a hair curling rollers with a diameter of over 13 millimeter are required. The reaction time of the hair shaping composition on the hair for the permanent shaping as well as for the permanent decurling takes about 30 minutes, depending on the condition of the hair and the desired degree of shaping. The reaction time may be shortened by a heat supply, for example, by using a heat radiator or a drying cap.

After the required reaction time of the hair shaping agent the rolled hair is rinsed with water and with a watery solution of an oxidation substance, preferably with a 2% hydrogen peroxide solution by reestablishing the previously cracked disulfide bonds of the hair keratin and is then fixed in the new shape.

Thereby, the reaction time of the fixing substance customarily is about 10 to 15 minutes. Finally, the rollers are removed and the hair is thoroughly rinsed with water.

Since the hair grows by about 1 to 2 cm a month, the permanent shape must be repeated after about 3-4 months. However, very often the hair is still in very good shape from the last permanent shape with respect to its deformation, so that a selective reshaping of the regrown hair at a length of 3 to 8 cm would suffice for reestablishing the hair-do.

However, hitherto no practicable process exists for a separate treatment of the unshaped hair regrowth and the still sufficiently shaped hair length. However, if the shaping treatment is extended to the full length, the already shaped hair portion is particularly subjected to stress, that is, increasingly with respect to the hair tip. Hair damage is not only caused in that the hair toward the tip had been already shaped repeatedly, but mainly because it is exposed longer to environmental influences (for example, sun) and had been more strongly stressed mechanically (for example, by combing).

From German Laid Open Pat. No. 1 467 853 it is known to moisten the hair before rolling it on permanent wave rollers with a liquid preneutralisation composition which contains an oxidation agent and which is additionally adjusted to a pH-value in the acid range. However, a selective treatment of the regrown hair cannot be obtained since the permanent wave liquid penetrates the whole roller. Moreover, the particularly stressed and sensitive hair tips are subjected for a long time to the effect of the oxidation substance and are also damaged in this manner. The use of so-called tip paper (thereby the hair tips are placed between a folded sheet which additionally may be impregnated with hair protecting or hair caring substances) is cumbersome and time consuming. Moreover, this enables only a protection of the hair tips, but not the remainder of the already shaped hair length.

Therefore, it was an object to find a process for the sole shaping of the hair regrowth without a substantial effect of the reductive permanent shaping substance on the already shaped hair areas.

It had been found that the objective is achieved in an exellent manner by a process for the selective permanent shaping of the hair regrowth, whereby the hair is at first treated with a liquid aqueous pretreatment composition, is rolled onto rollers, treated with a aqueous reducing permanent shaping composition, rinsed, and neutralized oxidatively, characterized in that the pretreatment composition and the permanent shaping composition form a separating layer at the contact face during contact, thus making an admixture of the pretreatment composition with the permanent shaping composition.

The reducing permanent shaping substance penetrates into the uppermost layer of the rolled hair and immediately forms a separating layer by reaction with the pretreatment layer which prevents a further penetration of the permanent shaping agent in deeper layers of the rolled hair. Thus, a selective shaping of the hair regrowth, which forms the uppermost layer of the roller, is thereby possible.

The process in accordance with the invention may be performed with different combinations of pretreatment substances and permanent shaping substances. The only prerequisite is that the pretreatment substance forms a separating layer during contact with the permanent shaping substance which prevents a further penetration of the permanent shaping substance into the inner layers of the rolled hair.

Preferably, the pretreatment substance contains a substance which is soluble or dispersable in a weak acid to neutral solution and results in a gel or a precipitation at a weak alkalic pH-value. After the hair is thoroughly moistened with the pretreatment substance and had been rooled onto rollers, a aqueous reducing alkali permanent shaping composition of pH$\pm$7,5 to 11 is applied on the rolled hair. A separating layer in form of a gel or a precipitation is formed in the outermost layer of the rolled hair during the contact of the alkali permanent shaping substance with the pretreatment substance which prevents a deeper penetration of the shaping substance into the inner layers of the hair or makes it more difficult to penetrate.

As substances which are soluble in weak acid solution or which result in a gel or a precipitation in a weak alkaline pH-value, particularly pysiologically acceptable high polymers, natural or synthetic polycarboxylic acid polymers, that is macromolecular compounds which are structured either totally or partially from monomer units containing a free carboxylic acid group are taken into consideration. In particular alginic acid is mentioned as a natural polycarboxylic acid polymer. Particularly suitable synthetic polymers, which consist totally of monomer units with a free carboxylic acid group are, for example, physiologically acceptable high polymeric, homopolymerisates of the acrylic acid and the methacrylic acid. Examples for macromolecular compounds, which are partially structured of monomer units with a free carboxylic acid group are highly polymerized co-polymerizates of acrylic acid and/or methacrylic acid with acrylic acid or methacrylic acid esters, acrylic or methacrylic acid amides, acrylic acid or methacrylic acid imides, crotonic acid, vinyl acetate, styrol or other vinyl or allyl derivatives, whereby at least 25 Mol % of the polymerisate consists of units containing carboxylic acid groups. In particular the pretreatment substance may be a aqueous dispersion of a high molecular copolymerisate of acrylic acid/methacrylic acid or acrylic acid/acrylic acid ester or acrylic acid/methacrylic acid ester or methacrylic acid/acrylic acid ester or methacrylic acid/methacrylic acid ester, whereby the mentioned esters are, in particular the methyl-, ethyl-, or butyl ester. Copolymerisates of methacrylic acid and acrylic acid ester are sold, for example, by the Firma Röhm GmbH, Darmstadt, under the trade name ROHAGIT ®. These polymersitates may be obtained in powder form (ROHAGIT S) as well as in form of a aqueous dispersion (ROHAGIT SD 15) in commerce.

The formation of an insulating gel like separating layer between the pretreatment composition and the permanent shaping composition can be easily illustrated by an experiment, whereby in a test tube of a 14 mm diameter about 5 cm$^3$ of a clear permanent shaping liquid A (from example 1) are overlayered with about 5 cm$^3$ of a clear pretreatment substance in accordance with example 5 in a very careful manner by using a pipette, for example. A 5 mm thick turbid gel like layer is formed at the phase border preventing an admixture of the pretreatment composition with the permanent wave composition.

A further possibility for performing the process in accordance with the invention consists in that a composition is used at first as the pretreatment composition which contains at least a physiologically acceptable organic or inorganic salt which is soluble or dispersible in a weak acid to neutral watery solution and which results in a gel or a precipitation at a weak alkalic pH-value and that a aqueous reducing alkalic permanent shaping substance of pH=7.5 to 11 is used, as already described above.

Examples for suitable salts are aluminum acetate, ammonium aluminium sulfate and ammonium cernitrate. Salts of macromolecular compounds are also considered, as far as they meet the aforementioned requirements. For example, physiologically compatible water soluble salts of the chitosana like, for example, chitosan asparaginate, chitosan lactate, chitosan acetate.

In the process in accordance with the invention the substance should be used which is soluble or dispersible in weak acid to neutral aqueous solution and which results in a gel or a precipitation at a weak alkalic pH-value in a concentration of about 1 to 10% by weight, preferably 2 to 6% by weight.

The hitherto described embodiments of the process in accordance with the invention are based on the principle to precipitate a substance contained in the pretreatment substance due to the alkalininity of the permanent shaping substance or to cause it to form a gel. However, the process described here may also be performed in a manner in that the pretreatment composition and the permanent composition each contain a substance which are so selected that they form a gel or a precipitation in combination with each other in a aqueous solution, independent from the pH-value of the solution. In this case it is not required that the pH-value of the permanent shaping substance used is in the alkaline range.

For example, the pretreatment substance may contain alginic acid or alkali alginates, while the permanent shaping composition contains a water soluble, physiologically acceptable salt of the calcium for example CaCl$_2$. A separating layer of gel like calcium alginate is formed during contact of the permanent shaping composition with the pretreatment composition.

A further embodiment of the process consists in that a composition is used as the pretreatment composition containing a cationic polymer, while the permanent shaping composition contains an anionic polymer. Naturally, both components may be exchanged with each other without any disadvantages, so that the cationic polymer is contained in the permanent shaping composition, while the anionic polymer is a component of the pretreatment composition. The cationic polymer together with the anionic polymer in a aqueous solution results in a precipitate which acts in a desired manner as a separating layer. The anionic and the cationic polymer should be present in the pretreatment composition or the permanent shaping composition in an amount of about 0.5 to 3.0% by weight, whereby an equimolar ratio is advantageous, but not necessarily required. Suitable anionic polymers are, for example, copolymerisates from crotonic acid, vinyl acetate and acrylic acid.

Examples for suitable cationic polymers are dimethyl diallyl ammonium chloride-homopolymer as well as copolymerisates from vinylpyrrolidon and diamethyl amino-ethyl methacrylate which are quaternized with dimethyl sulfate.

Moreover, it is possible to combine the aforementioned embodiments, so that for example an acid composition is used as the pretreating, composition which cantains a water soluble aluminum salt, like ammonium sulfate. (soluble in a weak acid solution, forming a gel like precipitate of aluminum hydroxide in the alkalic medium) as well as a cationic polymer like, for example, dimethyl diallyl ammonium chloride-homopolymerisate, and finally an alkalic permanent shaping substance is used with a content of an anionic polymer. A further example is example 7. During contact of the permanent shaping composition with the pretreating composition the formation of the separating layer occurs in two ways; once by the aluminum salt in the alkali medium and secondly by the precipitate which is formed by the anionic polymer with the cationic polymer. The presence of both substances in one pretreating composition has the further advantage that the pretreating composition can be used in combination with an alkaline permanent shaping composition as well as in combination with a nonalkaline one, which however contains a permanent shaping composition an anionic polymer.

Although, one can use the process in accordance with the invention with a good result with a pretreating composition of the aforementioned type which in a watery solution, emulsion or dispersion contains a substance which results in a gel or a precipitation during contact with the permanent shaping composition, it is particularly advantageous to use a pretreating composition which in addition contains at least a substance from the following listed substance groups a, b, c or d, which are also capable to neutralize alkaline permanent shaping agents, to remove reduction substance residues from the hair, to prevent a swelling of the hair or which have a caring effect on the hair.

(a) The pretreatment composition used by the described process may additionally contain a physiologically compatible weak acid, for example, citric acid, tartaric acid, lactic acid, acetic acid and phosphoric acid, or may contain acid phosphates for adjusting an acid pH-value, in particular when using an alkalic permanent shaping composition. The pretreatment substance may also contain buffer substances, for example, neutral or acidic amino acids.

(b) Furthermore, the pretreatment composition may additionally contain sodium bromate, aconitic acid, acetylene dicarboxylic acid, ethylene dicarboxylic acid, ethylmaleic acid, α ethyl crotonic acid, i-amylmaleic acid, angelic acid, n-butyl fumaric acid, n-and i-butyl maleic acid, citraconic acid, crotonic acid, fumaric acid, transglutaconic acid, isopropyl maleic acid, itaconic acid, maleic acid, mesaconic acid, α-methyl itaconic acid, cis-B, methyl glutaconic acid, trans-α-methyl glutaconic acid, propiolic acid or cinnamic acid for eliminating of reduction substance components which may penetrate into the rolled hair during the rinsing off of the reduction substance.

(c) It is also advantageous if the pretreatment composition contains substances which reduce the swelling of the hair. For this, one uses in particular alkali or earth alkali chlorides or sulfates. However care should be taken that when using calcium salts the pretreatment substance should not simultaneously contain alginic acid or alginates.

(d) The pretreatment composition maya additionally contain as a grooming substance, for example, lanolin, lecithin, proteins, glycerin, betain, allantoin, purcellin oil, silicon oil, spermaceti, fatty alcohols, wool wax, paraffin oil, beeswax, low boiling isoparaffins or silicon oils as well as urea, protein-fatty acid condensate or nonionic or amphoteric capillary active substances.

Naturally, the pretreatment composition may also contain in addition, if need be, customary cosmetic additives, for example, dyes, pigments, perfume oils, emulsifiers and others. The pH-value of the pretreatment substance is preferably 2 to 6.

Human hair which has about 3 to 8 cm long non-shaped hair regrowth is at first moistened with about 25-50 g of one of the aforementioned pretreatment composition in an even manner, depending on the fullness of hair, in accordance with the aforementioned process. The pretreatment composition may be present in a any given liquid aqueous form, for example, as a clear, colored or turbid solution, as a liquid emulsion or as a liquid dispersion. Thereafter, the hair is subsequently separated into strands and rolled onto rollers. The diameter of the roller is either 5 to 13 millimeter or more, depending whether a permanent shaping or a hair decurling is performed. About 40-60 g of a customarily liquid or thickened cream or gel like permanent shaping composition is applied onto the surface of the rollers, whereby it is either alkaline, depending on the composition of the pretreatment substance, if the pretreatment substance contains a substance which results in a gel or a precipitation in the alkaline range or which contains a substance resulting in a gel or a precipitation during the contact with the pretreatment composition due to the other aforementioned reasons.

The permanent shaping compositions which are useable in the subject described process are such on the basis of reduction substances, for example, sulfite or certain mercapto compounds, in particular salts or derivatives of the thioglycolic acid as ammonium thioglycolate as well as ammonium thiolactate, glycerin monothioglycolate or cystein and its derivatives. These permanent shaping compositions contain the reducing compounds in amounts normally used for hair shaping, for example, the ammonium salts of the thioglycolic acid or the thiolactic acid, in a concentration of about 2 to 12% by weight. The pH-value of the alkalic permanent shaping substances is generally at 7.5 to 11, whereby the adjustment is performed with ammonia, monoethanolamin, ammonium carbonate and/or ammonium hydrogen carbonate. At acid adjusted permanent shaping compositions (for example to pH=6.5–6.9) sodium or ammonium sulfite is preferably used as a reduction substance in a concentration of about 3 to 8% by weight (calculated as $SO_2$). These customary permanent shaping compositions may be directly used in combination with a pretreatment composition containing a substance which results as a gel or a precipitation in the alkaline medium, if they are alkaline adjusted (pH=7.5–11) if the shaping composition in accordance with the process described contains a substance which forms a gel or a precipitation only in combination with another defined substance, this defined other substance is then added to a customary permanent shaping base of a given pH-value in the range of 5 to 11. The corresponding possible combinations of substances were already previously stated.

The permanent shaping substance is rinsed off from the rollers with water after a reaction time sufficient for the permanent shaping of the hair which is about 5 to 25 minutes depending from the condition of the hair, the pH-value and the shaping efficiency of the permanent shaping composition, as well as in dependency from the application temperature. Subsequently, the rolled hairs are oxidatively fixed in the customary manner. The fixing serves to neutralize an excess of the shaping substance and to harden the softened hair. The oxidation substances which can be used in accordance with the invention are not specifically limited; and given oxidation substance may be used. Examples for such commercially available oxidation substances are potassium bromate, sodium bromate, sodiumperborate, hydrogen peroxide and urea peroxide. The concentration of the oxidation substances is variable in accordance with the hardening conditions, like temperature and time. Normally, the oxidation compositions are used in the watery fixing compositions in a concentration of about 0.5 to about 10.0% by weight. The oxidation substance is useable together with other known additives.

The permanent shaping compositions and fixing compositions usable in accordance with the inventive process may naturally contain additional additives which are commonly used in permanent shaping compositions and fixing compositions like, for example, hair conditioning substancees, hair grooming substances, dyes, perfume oils and others.

Finally the rollers are removed, the fixing substance is rinsed off from the hair and the hair is further treated in customary manner. Normally, subsequent to a permanent shaping of the hair the hair is set in a water wave. In case of a hair decurling one could proceed by rinsing off the fixing substance while the hair is still rolled and to subsequently dry the hair directly on the roller without removing them. Furthermore, it is also possible to immediatley dry blow the hair after removing the rollers and after rinsing off the fixing substance.

The subsequent examples should explain the subject matter of the invention more closely.

PERMANENT SHAPING

EXAMPLE 1

Combination: substance forming a gel in an alkaline solution/alkaline permanent waving composition A permanent waved hair of about 16 cm in length, whose hair regrowth is regrown smooth at a length of about 3 cm is washed with a shampoo, rinsed with water and thoroughly towel dried with a hand towel. Subsequently, the hair is thoroughly moistened with 30 g of a pretreatment composition being composed of

| | |
|---|---|
| 12.0 g | of a 30% watery dispersion of a copolymerisate of methacrylic acid and acrylic acid ethyl ester (commercial product ROHAGIT SD 15 of Firm Rohm GmbH,Darmstadt). |
| 1.0 g | betain monohydrate |
| 1.5 g | protein fatty acid condensate, 28% watery solution (Commercial product Lamepon S of the Chemischen Fabrik Grunau GmbH, Germany) |
| 0.5 g | polyethylene glycol-sorbitanmonolaurate |
| 85.0 g | water |
| 100.0 g | | and a pH=5.8. The moistened hair is separated into strands and rolled onto perment waving rollers with a diameter of 8 millimeter. 50 g of a permanent shaping preparation with the following composition A or B are applied on the rollers:

| (A) | | |
|---|---|---|
| | 23.6 g | ammonium thioglycolate, 50% watery solution |
| | 6.4 g | ammonium hydrogen carbonate |
| | 1.0 g | ammonium carbonate |
| | 0.4 g | octylphenol oxyethylated with 20 Mol ethylene oxide |
| | 2.0 g | dimethyl diallyl ammonium chloride-homopoly = merisate, 40% watery solution |
| | 0.4 g | perfume oil |
| | 66.2 g | water |
| | 100.0 g | |

This permanent waving liquid has a pH-value of 8.7.

| (B) | | |
|---|---|---|
| | 20.0 g | ammonium thioglycolate, 50% watery solution |
| | 4.0 g | ammonia, 25% watery solution |
| | 6.0 g | cetylstearylalcohol |
| | 1.0 g | sodium laurylsulfate |
| | 1.0 g | perfume oil |
| | 68.0 g | water |
| | 100.00 | |

This permanent shaping cream ha s a pH-value of 9.6.

After a reaction time of 15 minutes the rolled hair is thoroughly rinsed with lukewarm water. Surplus water is removed with a towel or a paper napkin. Subsequently. 50 g of a fixing preparation of the following composition which has a pH-value of 2.2 is applied on the rolled hair.

| | |
|---|---|
| 4.0 g | hydrogen peroxide, 50% watery solution |
| 0.2 g | phosphoric acid, 85% |
| 1.0 g | citric acid |
| 94.8 g | water |
| 100.0 g | |

After a reaction time of 5 minutes the hairs were removed from the rollers, the fixing preparation was removed by rinsing with water and the hair is set in customary manner in a water wave and dried. A uniform curled hair from the hair root to the hair tip, whereby the previously curled hair was not part of the shaping and was therefore not again chemically damaged.

EXAMPLE 2

The permanent shaping of the regrowth of the hair is performed as described in example 1, however a pretreatment preparation with the following composition is used:

| | |
|---|---|
| 15.0 g | of a 28% aqueous dispersion of a copolymerisate of acrylic acid and acrylic acid ethyl ester (Commercial product Primal ASE 60 of Firma Rohm & Haas Co. Inc., USA) |
| 10.0 g | glycerin |
| 1.0 g | lactatic acid, 90% |
| 0.5 g | d,L-methionin |
| 1.0 g | L-glutaminic acid |
| 1.0 g | 1,4-nonylphenol, with 10 Mol ethylenoxide oxethi = lized |
| 0.5 g | perfume oil |
| 71.0 g | water |
| 100.0 g | |

The pH-value of this liquid dispersion is 2.6.

EXAMPLE 3

The permanent shaping of the regrowth of the hair is performed as described in example 1, however a pretreatment preparation of the following composition is used:

| | |
|---|---|
| 2.0 g | chitosan with 90% free amino groups |
| 1.0 g | lactatic acid, 90% |
| 2.0 g | sodium bromate |
| 95.0 g | water |
| 100.0 g | |

The pH-value of this solution is 5.1.

EXAMPLE 4

The permanent shaping is performed for the hair regrowth as described in example 1, however a pretreatment preparation of the following composition is used:

| | |
|---|---|
| 5.0 g | aluminum sulfate, $Al_2(SO_4)_3$ |
| 1.5 g | cetylstearylalcohol |
| 0.2 g | sodium laurylsulfate |
| 0.5 g | polyethylene glycol-sorbitan monolaurate |
| 0.3 g | perfume oil |
| 92.5 g | water |
| 100.0 g | |

The pH-value of this liquid emulsion is 3.

EXAMPLE 5

The permanent shaping of the hair regrowth is performed as described in example, however a pretreatment preparation of the following composition is used:

| | |
|---|---|
| 3.0 g | ammonium aluminum sulfate $NH_4Al(SO_4)_2 \cdot 12H_2O$ |
| 2.0 g | trimethyl cetlyamonnium chloride, 25% watery solution |
| 1.5 g | sodium chloride |
| 1.0 g | glycin |
| 0.3 g | 1,4-nonylphenol, oxyethylated with 10 Mol ethylene oxide |
| 0.2 g | perfume oil |
| 92.0 g | water |
| 100.0 g | |

The pH-value of this clear solution is 3.5.

EXAMPLE 6

Combination: pretreatment composition with anionic polymer/permanent shaping composition with cationic polymer Already permanently shaped hair of 12 cm in length, which still have a sufficient curling, whose regrowth of hair is about 4 cm smooth is washed, rinsed and towel dried. Subsequently, the hair is thoroughly moistened with 30 g of a pretreatment preparation of pH=7.2 of the following composition:

| | |
|---|---|
| 6.0 g | 60% solution of a mixed polymerisate of vinyl acetate crotonic acid and acrylic acid in water/isopropanol (1:4) [anionic polymer] |
| 3.0 g | glycerin |
| 1.0 g | sodium bromate |
| 0.3 g | ammonia, 25% watery solution |
| 89.7 g | water |
| 100.0 | |

The moistened hair is separated into strands and rolled onto permanent rollers with a 6 millimeter diameter. Subsequently 50 g of a permanent shaping preparation with a content of a cationic resin of the composition A (from example 1) or C are applied

| | | |
|---|---|---|
| (C) | 2.0 g | of a 50% watery solution of a copolymerisate of 80% vinylpyrrolidon/20% dimethyl aminoethyl methacrylate, partially quaternized with dimethyl = sulfate (median molecular weight = 100 00) [cationic polymer] |
| | 24.6 g | ammonium thiolactate, 50% watery solution |
| | 4.0 g | ammonia, 25% watery solution |
| | 0.5 g | 1,4-nonylphenol, oxethylized with 10 Mol ethylene oxide |
| | 0.2 g | perfume oil |
| | 68.7 g | water |
| | 100.0 g | |

This permanent shaping preparation has a pH-value of 9.6.

After a reaction time of 12 minutes the rolled hair is thoroughly rinsed with lukewarm water. The excess water is removed with a towel. Subsequently, 50 g of a customary fixing composition on the basis of hydrogen peroxide, for example a 2% watery $H_2O_2$-solution is applied to the rolled hair. After a reaction time of 3 minutes the hair is removed from the rollers, is moistened with further 30 g of the fixing composition and is thoroughly rinsed after 2 minutes. Finally, the hair is set to a water wave in a customary manner and dried.

EXAMPLE 7

Combination: pretreatment composition with cationic polymer/permanent waving composition with anionic polymer The procedure is the same as described in example 6, however a pretreatment preparation of the following composition is used

| | |
|---|---|
| 7.5 g | potassium aluminum sulfate, $KAl(SO_4)_2 \cdot 12H_2O$ |
| 3.5 g | dimethyl diallyl ammonium chloride-homopolymerisate, median molecular weight = 500 00, 40% watery solution [cationic polymer] |
| 1.0 g | maleic acid |
| 1.0 g | 1,4-nonylphenol, oxethylized with 10 Mol ethylene oxide |
| 0.2 g | allantoin |
| 0.3 g | perfume oil |
| 86.5 g | water |
| 100.0 g | |

The pH-value of this liquid pretreatment composition is 2.0; and a permanent shaping composition of the composition

| | |
|---|---|
| 3.5 g | 60% solution of a copolymerisate of vinyl acetate, crotonic acid and acrylic acid in water/isopropanol (1:4) [anioinic polymer] |
| 13.0 g | ammonium thioglycolate, 50% watery solution |
| 2.0 g | ammonium carbonate, $(NH_4)_2CO_3$ |
| 1.0 g | ammonium hydrogen carbonate $NH_4HCO_3$ |
| 0.5 g | octylphenol, oxethylized with 20 Mol ethylene oxide |
| 0.3 g | perfume oil |
| 79.7 g | water |
| 100.0 g | |

This permanent shaping composition has a pH-value of 8.8.

DECURLING

During decurling one principally can follow analog to the examples 1 to 7, whereby roller with a diameter of over 20 millimeters have to be used. A further example is described in the following.

EXAMPLE 8

A 15 cm long smooth hair which had been decurled 3 months before, whose hair regrowth is regrown at a length of about 4 cm and is very curled is moistened with 30 g of a pretreatment preparation which is present as a liquid emulsion and has a pH-value of 3 and which has the following composition

| | |
|---|---|
| 5.0 g | aluminum sulfate, $Al_2(SO_4)_3$ |
| 1.5 g | cetylstearylalcohol |
| 0.2 g | sodium laurylsulfate |
| 0.5 g | polyethylene-sorbitan monolaurate |
| 0.3 g | perfume oil |
| 92.5 g | water |
| 100.0 g | |

Subsequently the hair is rolled to rollers with a 24 millimeter diameter. 50 g of a permanent shaping preparation in form of a cream of composition B (from example 1) are applied on the rollers. After a reaction time of 20 minutes the rolled hair is rinsed with water and is the treated with 50 g of a fixing preparation whose pH-value is 6.8 and which has the following composition

| | |
|---|---|
| 8.0 g | sodium bromate |
| 2.0 g | of a 50% watery solution of a compolymerisate of 80% vinylpyrrolidon/20% dimethyl aminoethyl methacrylate, partially with dimethyl sulfate quaternized (median molecular weight = 100 00) |
| 90.0 g | water |
| 100.00 | |

After a reaction time of 10 minutes the rollers are removed. Finally, the hair is thoroughly rinsed with water and blow dried. After this treatment the hair is uniformly smoothed from the roots to the tip by preserving the hair structure.

We claim:

1. Process for a selective permanent shaping of the regrowth of hair, whereby the hair is at first treated with a liquid aqueous pretreatment composition, rolled onto rollers, treated with an aqueous reducing permanent shaping composition, rinsed and neutralized oxidatively, characterized in that the pretreatment composition and the permanent shaping composition form a separating layer at their contact face during contact, thus making an admixture of the pretreatment composition with the permanent shaping composition more difficult or preventing the same.

2. Process in accordance with claim 1, characterized in that a liquid aqueous compound is used as the pretreatment composition which contains at least one physiologically acceptable composition which is soluble or dispersible in weak acid to neutral aqueous solution and which results in a gel or precipitation at a weak alkaline pH-value, and that a watery reducing permanent shaping composition of a pH=7.5 to 11 is used.

3. Process in accordance with claim 2, characterized in that a pretreatment composition is used which contains the physiologically acceptable substance which is soluble or dispersible in weak to neutral aqueous solution and which results in a gel or a precipitation at a weak alkalic pH-value in an amount of 1 to 10% by weight.

4. Process in accordance with claim 1, characterized in that a aqueous preparation is used as the pretreatment composition which contains alginic acid or an alkali alginate and which uses as a permanent shaping composition a aqueous compound on the basis of a hair keratin reducing substance containing a water soluble salt of the calcium.

5. Process in accordance with claim 1, characterized in that a aqueous preparation is used as the pretreatment composition which contains an anionic polymer and which uses as a permanent shaping preparation a composition which contains a cationic polymer.

6. Process in accordance with claim 5, characterized in that the cationic polymer and the anionic polymer are used in a concentration of 0.5 to 3.0% by weight in the pretreatment or the permanent shaping composition.

7. Process in accordance with claim 6, characterized in that a copolymerisate of vinyl acetate, crotonic acid and acrylic acid are used as an anionic polymer.

8. Process in accordance with claim 7, characterized in that a copolymerisate of vinylpyrroidon and dimethyl aminoethyl methacrylate is used as a cationic polymer which is quaternized with dimethyl sulfate, or a dimethyl diallyl ammoinum chloride-homopolymerisate.

9. Process in accordance with claim 1, characterized in that a aqueous preparation is used as a pretreatment composition which contains a cationic polymer and that a preparation is used as the permanent shaping composition which contains an anionic polymer.

10. Process in accordance with claim 9, characterized in that the cationic polymer and the anionic polymer are used in a concentration of 0.5 to 3.0% by weight in the pretreatment or the permanent shaping composition.

11. Process in accordance with claim 1, characterized in that a pretreatment composition is used which additionally contains at least one of the weak acids, citric acid, tartaric acid, lactactic acid, phosphoric acid, acetic acid or acid phosphates or neutral or acid amino acids.

12. Process in accordance with claim 1, characterized in that a pretreatment composition is used which in addition contains sodium bromate, aconitic acid, acetylen dicarboxylic acid, ethylene dicarboxylic acid, ethylmaleic acid, α-ethyl crotonic acid, i-amylmaleic acid, angelic acid, n-butyl fumaric acid, n- and i-butylmaleic acid, citraconic acid, crotonic acid, fumaric acid, transglutaconic acid, isopropyl maleic acid, itaconic acid, maleic acid, mesaconic acid, α-methylitacononic acid, cis-β-methyl glutaconic acid, trans-α-methyl glutaconic acid, propiolic acid or cinnamic acid.

13. Process in accordance with claim 1, characterized in that a pretreatment composition is used which in addition contains lanolin, lecithin, protein, glycerin, betain, allantoin, purcellin oil, silicon oil, spermaceti, fatty alcohol, wool wax, paraffin oil, bee wax, low boiling isoparaffins or silicon oils or nonionic or amphoteric capillary active substances.

14. Pretreatment substance for performing the process in accordance with claim 13, characterized in that it contains a water soluble aluminum salt and a cationic polymer.

15. Substance in accordance with claim 14, characterized that it has a pH-value of 2 to 6.

16. Process in accordance with claim 2, characterized in that a pretreatment substance is used which contains at least one physilogically acceptable substance, selected from physiologically acceptable natural or synthetic carboxylic acid polymers sturctured totally or partially from monomer units containing a free carboxylic acid group.

17. Process in accordance with claim 16, characterized in that a pretreatment substance is used which contains alginic acid or a physiologically acceptable high polymeric homopolymer of the acrylic acid or the methacrylic acid.

18. Process in accordance with claim 16, characterized in that a pretreatment composition is used which contains a highly polymerized Co-polymerisate of acrylic acid and/or methacrylic acid with acrylic acid- or methacrylic acid esters, acrylic acid- or methacrylic acid amides, acrylic acid- or methacrylic acid imides, crotonic acid, vinyl acetate, styrol or other vinyl- or allyl derivatives, whereby at least 20 Mol % of the polymerisate consits of units containing the carboxylic groups.

19. Process in accordance with claim 16 characterized in that a pretreatment composition is used which contains a high molecular copolymerisate of acrylic acid/methacrylic acid or acrylic acid/acrylic acid ester or methacrylic acid/acrylic acid ester or methacrylic acid/methacrylic acid ester, whereby the mentioned esters are in particular the methyl-, ethyl-, propyl- or butyl ester.

20. Process in accordance with claim 2, characterized in that a preparation used as a pretreatment composition which contains at least one physiologically acceptable substance, selected from physilogically acceptable organic or inorganic salts which are soluble or dispersible in a weak to neutral aqueous solution and result in a gel or a precipitation at a weak alkaline pH-value.

21. Process in accordance with claim 20, characterized in that aluminum acetate, ammonium aluminum sulfate or ammonium cernitrate is used as a physilogically organic or inorganic salt.

22. Process in accordance with claim 20, characterized in that a compound is used as the pretreatment substance which contains a water soluble physiologically acceptable chitosan.

23. Process in accordance with claim 22, characterized in that a pretreatment composition is used which contains the physiologically acceptable composition which is soluble or dispersible in weak to neutral aqueous solution and which results in a gel or a precipitation at a weak alkaline pH-value in an amount of 1 to 10% by weight.

* * * * *

UNITED STATES PATENT AND TRADEMARK OFFICE
CERTIFICATE OF CORRECTION

PATENT NO. : 4 660 580  Page 1 of 2
DATED : April 28, 1987
INVENTOR(S) : Dietrich Hoch, Theodor Wajaroff and Eugen Konrad It is certified that error appears in the above-identified patent and that said Letters Patent are hereby corrected as shown below:

In column 2, line 35, after (composition) cancel "." and add --more difficult or preventing the same.--

In column 3, line 61 cancel "chitosana" and substitute --chitosan--

In column 5, line 40, after (may) cancel "a"

In column 6, line 30, after (pH=7.5-11) cancel "if" and substitute --.If--

In column 9, line 4, after (example) insert --1--

In column 11, line 1, after (is), seccond occurrance, cancel "the" and substitute --then--

In column 11, line 66, cancel "vinylpyrroidon" and substitute --vinylpyrrolidon--

In Column 12, line 1, cancel "ammoinum" and substitute --ammonium--

In column 12, line 44, cancel "physikigically" and substitute --physiologically--

In column 12, line 61, cancel "20" and substitute --25--

UNITED STATES PATENT AND TRADEMARK OFFICE
CERTIFICATE OF CORRECTION

PATENT NO. : 4,660,580     Page 2 of 2

DATED : April 28, 1987

INVENTOR(S) : Dietrich Hoch, Theodor Wajaroff and Eugen Konrad

It is certified that error appears in the above-identified patent and that said Letters Patent is hereby corrected as shown below:

In column 14, lines 1 + 2, cancel "physilogically" and substitute --physiologically acceptable--

Signed and Sealed this

Twelfth Day of January, 1988

Attest:

DONALD J. QUIGG

*Attesting Officer*     *Commissioner of Patents and Trademarks*